United States Patent [19]

Zwijnenburg

[11] Patent Number: 4,824,320

[45] Date of Patent: Apr. 25, 1989

[54] DEVICE FOR PICKING UP, DISPLACING AND DELIVERING PRODUCTS

[75] Inventor: Jan Zwijnenburg, Almelo, Netherlands

[73] Assignee: U.S. Philips Corporation, New York, N.Y.

[21] Appl. No.: 160,423

[22] Filed: Feb. 25, 1988

[30] Foreign Application Priority Data

Mar. 30, 1987 [NL] Netherlands ............... 8700735

[51] Int. Cl.⁴ ............................................. G66C 23/00
[52] U.S. Cl. .................................... 414/744.3; 74/96; 74/479; 901/22
[58] Field of Search ........... 414/744 R, 744 A, 744 B, 414/744 C; 901/22; 74/749, 96, 25

[56] References Cited

U.S. PATENT DOCUMENTS

| | | | |
|---|---|---|---|
| 3,134,263 | 5/1964 | Jong | 73/864.25 |
| 3,252,327 | 5/1966 | Ferrari | 73/864.25 |
| 4,343,766 | 8/1982 | Sisti et al. | 422/63 |
| 4,589,818 | 5/1986 | Brown et al. | 414/744 A |
| 4,665,558 | 5/1987 | Burke | 901/22 X |

Primary Examiner—Robert J. Spar
Assistant Examiner—Donald W. Underwood
Attorney, Agent, or Firm—Paul R. Miller

[57] ABSTRACT

A device for the exchange of specimens, for example for X-ray analysis, comprises a bush which is secured to a piston accommodated in a cylinder so that displacement of a pressurized fluid in the cylinder displaces the piston and the bush parallel to a center line of the bush. When structure for restricting the displacement are provided, the specimens can be exchanged between two positions to be selected.

9 Claims, 2 Drawing Sheets

DEVICE FOR PICKING UP, DISPLACING AND DELIVERING PRODUCTS

This invention relates to a device for picking up, displacing and delivering products in analysis apparatus, comprising a rod which is supported in a bush and which is reciprocatable in its longitudinal direction and rotatable about its centre line, to the rod there being connected a supporting member for handling the products which extends transversely of the rod as well as an arm which extends outwards from the rod and which is coupled to an adjusting arm which is rotatable, by means of a drive member, about an axis of rotation which extends parallel to the centre line of the rod, there also being provided drive means for reciprocation of the rod in its longitudinal direction.

A device of this kind is known from U.S. Pat. No. 3,134,263. At one end of the rod of the known device there is provided a disk comprising a groove which is engaged by pins secured to a fork-shaped bracket which is connected to an arm which can be pivoted by means of a cam mechanism, against spring force, for reciprocation of the rod in its longitudinal direction. This mechanism has a rather complex construction, is subject to substantial wear and produces a substantial amount of noise.

It is the object of the invention to provide a device of the kine set forth in which the drawbacks of the known construction are avoided.

In accordance with the invention, this object can be achieved in that the bush which supports the rod is secured to a piston accommodated in a cylinder so that the piston and the bush can be displaced parallel to the centre line of the bush by admitting and/or extracting pressurized liquid to and from the cylinder, there being provided means for restricting the displacement of the rod with respect to the bush in at least one direction.

The device having the construction in accordance with the invention is simpler and suitable for realizing a fast and uniform displacement of the rod in its longitudinal direction by means of the piston and the bush.

It is to be noted that in the device disclosed in U.S. Pat. No. 3,134,263, the supporting member for handling the products is formed by a nozzle for drawing liquids. However, it will be apparent that the supporting member can alternatively be formed by a projecting arm whereto means are connected, for example for gripping an object to be examined in an analysis apparatus, which means for gripping such an object can be formed by claws, magnets, suction cups an the like. It is to be noted that Netherlands Patent Application No. 6,717,101 (FIG. 9) corresponding to U.S. Pat. No. 3,497,320 discloses a device in which a nozzle for drawing and delivering liquid samples is secured to a rotatable head, the nozzle being movable up and down, parallel to the axis of rotation of the rotatable head, by means of a rack mechanism. The introduction of such a drivable rack mechanism in a rotatable head, however, again results in a complex mechanism.

The invention will be described in detail hereinafter with reference to an embodiment of the construction in accordance with the invention which is diagrammatically shown in the accompanying Figures.

Figure 1:
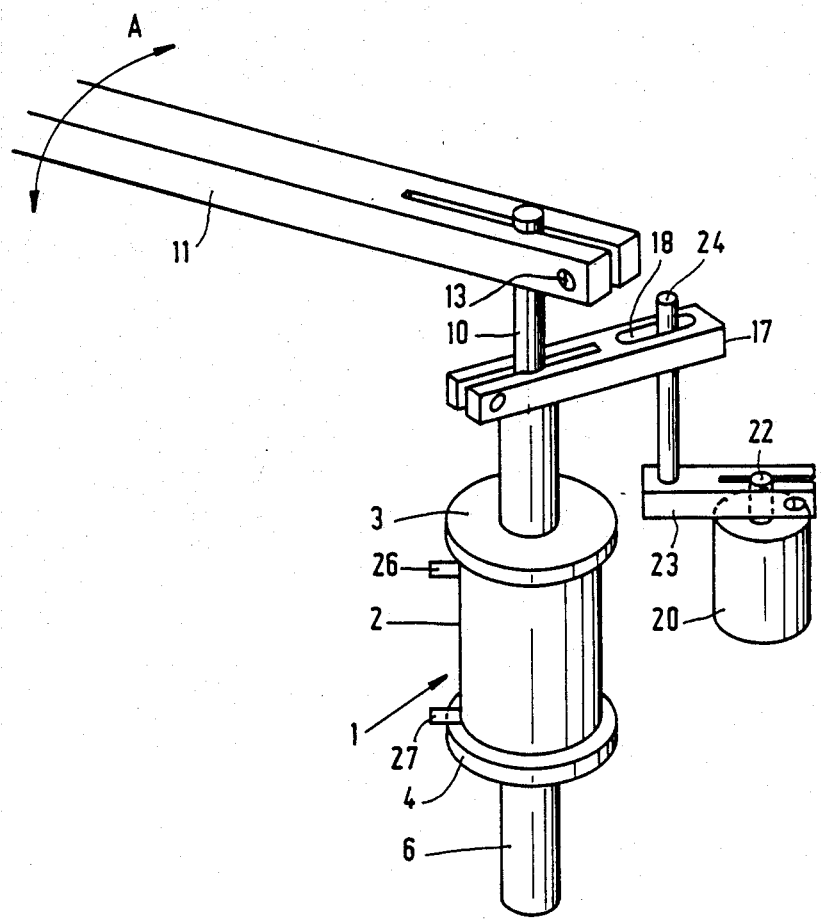
FIG. 1 is a diagrammatic perspective view of a device in accordance with the invention.

The device comprises an adjusting cylinder 1 which in the present embodiment consists of a jacket 2 which is closed at the top and the bottom by cylinder lids 3 and 4, respectively, each lid extending inside the cylinder jacket 2 over a part of its length. The adjusting cylinder is secured to a supporting member 5 which is only partly shown and which occupies a stationary position (see also FIG. 2).

In bores which are situated in an aligned position and which are provided in the cylinder lids 3 and 4 there is arranged a bush 6 which is slidable in its longitudinal direction with respect to the cylinder lids 3 and 4, so that the centre line of this bush coincides with the centre line of the cylinder jacket 2. A piston 7 which is situated within the cylinder jacket 2 is connected to the bush 6.

At the ends of the bush 6 there are provided bearing bushes 8 and 9 for supporting the rod 10 whose centre line coincides with the centre line of the bush 6. To the upper side of the rod 10 there is secured a supporting member 11 which extends perpendicularly to the rod 10 and whose end is provided with a gripping member 12 for picking up an object to be displaced.

Figure 2:
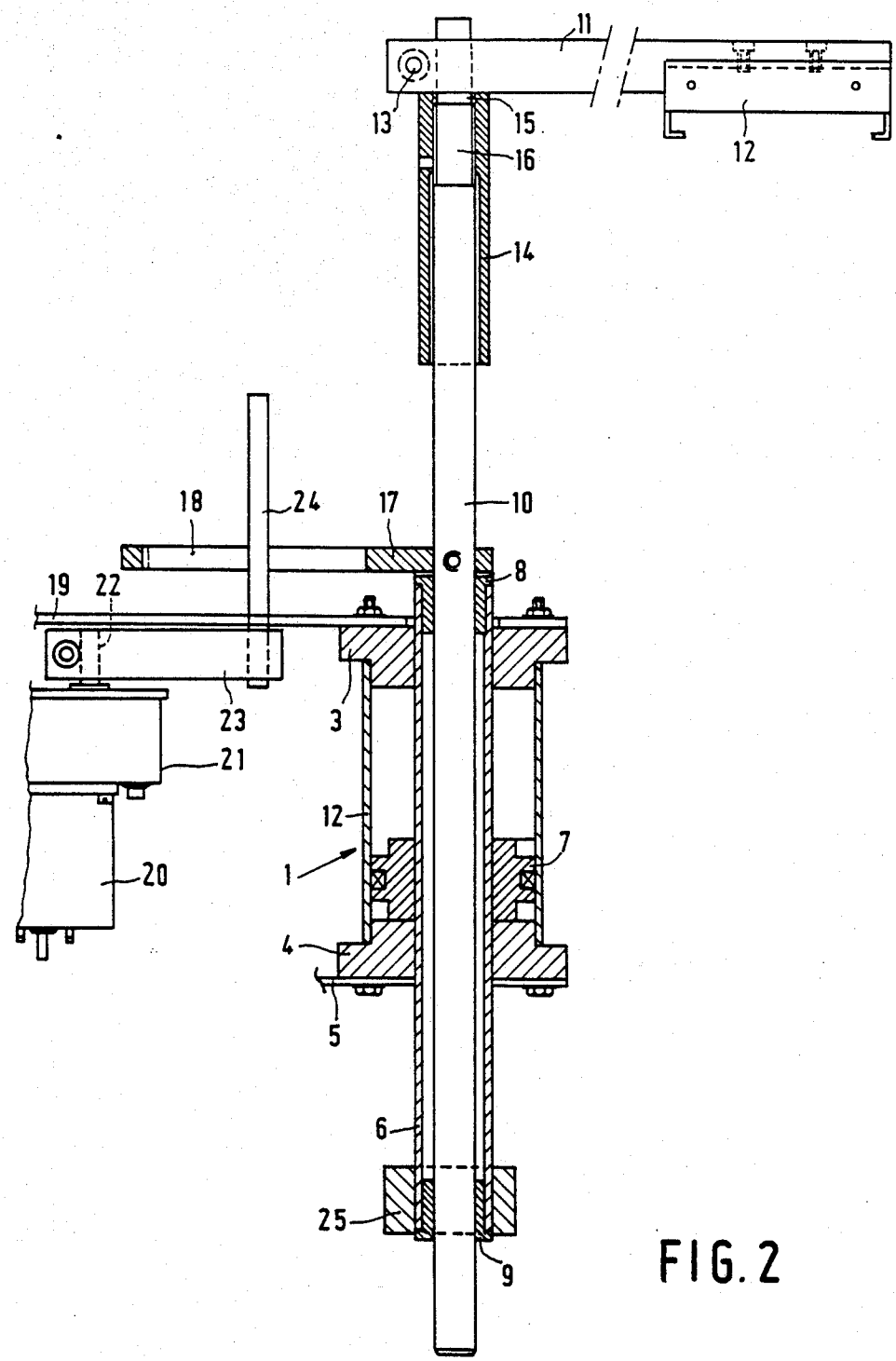
FIG. 2 is a sectional view at an increased scale of the device shown in FIG. 1.

As appears notably from FIG. 2, the end of the supporting member which is clamped to the upper end of the rod 10 by means of a clamping bolt 13 bears on the upper end of a bush 14 which is internally threaded over a part of its length and in which the threaded upper end 16 of the rod 10 is screwed. It will be apparent that the height position of the supporting member 11 can be simply adjusted by rotation of the bush 14 in order to clamp the supporting member onto the rod 10 by means of the clamping bolt 13.

Some distance below the supporting member 11 an arm 17 which extends radially with respect to the rod 10 is secured to the rod 10. A slotted hole 18 is provided in the free end of the arm 17.

The adjusting cylinder 1 also comprises a supporting plate 19 whereto an electric motor 20 with a gearbox 21 is secured. To the driving shaft 22 of the gearbox 21 there is clamped the end of an arm 23, a pin 24 which extends parallel to the rod 10 and which projects through the slotted hole 18 in the arm 17 being connected to the other end of the arm.

As appears notably from FIG. 2, a ring 25 which surrounds the bush is secured to the lower end of the bush 6.

As appears from FIG. 1, nozzles 26 and 27 are provided on the cylinder jacket 2 for the connection of ducts via which pressurized fluid can be admitted to and extracted from the cylinder space 2 above and below the piston 7.

The arm 23 supporting the pin 24 can be pivoted to and fro through a given angle by application of appropriate controls signals to the motor 20. It will be apparent that, because the pin 24 is situated in the slotted hole 18 provided in the arm 17, the pivoting to and fro of the arm 23 will be accompanied by a pivoting motion through a given angle of the arm 17 and hence of the rod 10 clamped to the arm 17 and the supporting member 11 secured to the rod 10, as denoted by the double arrow A in FIG. 1.

Moreover, the rod 10 can be moved upwards from the position shown in FIG. 1 by admitting pressurized liquid underneath the piston 7 arranged in the adjusting cylinder 1. When pressurized fluid is admitted underneath the piston 7, the piston 7 and the bush 6 secured thereto will be moved upwards in FIG. 2. The rod 10 is then taken along because the arm 17 bears on the upper end of the bush 6.

The piston 7 and the bush 6 connected thereto will be lowered again when fluid is allowed to escape from the part of the cylinder space 2 which is situated underneath the piston 7 and when (possibly pressurized) fluid is admitted to the space above the piston 7. The rod 10 and the supporting member connected thereto will follow this downward movement under the influence of the force of gravity. However, the rod 10 can alternatively be coupled to the bush 6 so that the rod 10 is rotatable with respect to the bush but not slidable in its longitudinal direction with respect to the bush, so that the bush is positively taken along by the bush 6 also in the downward direction.

As has already been stated, the described device can be used particularly effectively, for example for displacing specimens to be examined in an X-ray analysis apparatus or the like. In a first position of the supporting member, a specimen will then be gripped by the gripping member 12 or be arranged in the gripping member, after which the specimen is lifted by the rising of the rod 10 with the supporting member 11 as shown in FIG. 2. Subsequently, the supporting member can be rotated through the desired angle by activation of the motor 20, after which the rod 10 with the supporting member 11 is lowered to a position suitable for delivering the specimen. After the specimen has been delivered, the supporting member can be returned to the first position by performing the described displacements in the reverse order. Thus, an arbitrary number of specimens can be fully automatically examined, for example in an X-ray analysis apparatus.

The stroke can be readily influenced by securing the arm 17 and/or the ring 25 on the bush in the desired locations.

In order to restrict the reciprocating motion, for example adjustable abutments (not shown) can be provided in order to limit, for example the pivoting of the arm 23.

The arm 22 of the described embodiment reciprocates under the influence of the drive motor 20. However, it is alternatively possible to construct the transmission formed by the arm 23 and the pin/slotted hole link so that a desired reciprocating motion of the arm 11 is also realized when the motor rotates in only one direction.

It will be apparent that a plurality of modifications of and/or additions to the embodiment described with reference to the Figures are feasible within the scope of the present invention.

For example, the rod 10 an the sleeve bearings 8 and 9 accommodating the rod 10 may have a non-round cross-section, with the result that the rod will still be slidable in its longitudinal direction with respect to the bush, but the bush 6 and the piston 7 rotate together with the rod.

What is claimed is:

1. A device for picking up, displacing, and delivering products in analysis apparatus comprising
a rod being reciprocatingly displaced in a longitudinal direction, and said rod being rotatingly movable about said longitudinal direction,
supporting means connected to said rod for handling products, said supporting means extending transversely to said rod,
an adjustable arm extending outwardly from said rod,
motor means for driving said adjustable arm in rotation about an axis of rotation parallel to the center line of said rod,
drive means for reciprocating said rod in said longitudinal direction, said drive means including
   (a) a piston cylinder having means for admitting or extracting pressurized fluid to or from said piston cylinder,
   (b) a bush supporting said rod and extending through said piston cylinder to said adjustable arm,
   (c) a piston in said piston cylinder secured to said bush, said piston and said bush being displaceable parallel to the center line of said bush by admission or extraction of said pressurized fluid, and
   (d) means for restricting longitudinal displacement of said rod with respect to said bush in at least one direction.

2. A device according to claim 1, wherein said adjustable arm includes said means for restricting longitudinal displacement of said rod, said adjustable arm restricting downward movement of said rod with respect to said bush.

3. A device according to claim 1 or 2, wherein said adjustable arm is secured to said rod, said adjustable arm being slidable with respect to said rod, and said adjustable arm being locked to said rod at a desired position.

4. A device according to claim 3, wherein said bush includes an abutment member secured to said bush at a side of said piston cylinder remote from said adjustable arm, said abutment member being displaceable with respect to said bush in a longitudinal direction of said bush.

5. A device according to claim 4, wherein said rod is supported in said bush by sleeve bearings disposed near ends of said bush.

6. A device according to claim 5, wherein said supporting means bears on an upper end of a second bush, said second bush being screwed onto said rod, and said second bush being secured on said rod in a desired position.

7. A device according to claim 1 or 2, wherein said bush includes an abutment member secured to said bush at a side of said piston cylinder remote from said adjustable arm, said abutment member being displaceable with respect to said bush in a longitudinal direction of said bush.

8. A device according to claim 1 or 2, wherein said rod is supported in said bush by sleeve bearings disposed near ends of said bush.

9. A device according to claim 1 or 2, wherein said supporting means bears on an upper end of a second bush, said second bush being screwed onto said rod, and said second bush being secured on said rod in a desired position.

* * * * *